United States Patent [19]

Redmore

[11] 4,235,809
[45] Nov. 25, 1980

[54] α-AMINO PHOSPHONIC ACIDS

[75] Inventor: Derek Redmore, Ballwin, Mo.

[73] Assignee: Petrolite Corporation, St. Louis, Mo.

[21] Appl. No.: 713,705

[22] Filed: Aug. 12, 1976

[51] Int. Cl.$^3$ ............................................. C07F 9/38
[52] U.S. Cl. .................................. 260/502.5; 546/21
[58] Field of Search ...................................... 260/502.5

[56] References Cited

U.S. PATENT DOCUMENTS

| | | | |
|---|---|---|---|
| 2,635,112 | 4/1953 | Fields | 260/502.5 |
| 2,847,442 | 8/1958 | Sallmann | 260/502.5 |
| 3,288,846 | 11/1966 | Irani et al. | 260/502.5 |
| 3,424,788 | 1/1969 | Guttmann et al. | 260/502.5 |
| 3,549,728 | 12/1970 | Balde et al. | 260/502.5 |

FOREIGN PATENT DOCUMENTS 1125977  9/1968  United Kingdom ................... 260/502.5

OTHER PUBLICATIONS

Frank, "Chem. Rev. ", vol. 1, No. 4 (Aug. 1961), pp. 389–394.
The Merck Index, 6th ed. (1952), pp. 624, 625, R5356M524.

Primary Examiner—Joseph E. Evans
Attorney, Agent, or Firm—Sidney B. Ring; Hyman F. Glass

[57] ABSTRACT

This invention relates to the preparation of α-amino phosphonic acids by the direct addition of phosphorous acid to imines.

4 Claims, No Drawings

α-AMINO PHOSPHONIC ACIDS

Previous routes to α-aminophosphonic acids include (a) the addition of a diester of phosphorous acid to an imine followed by hydrolysis according to the following equation:

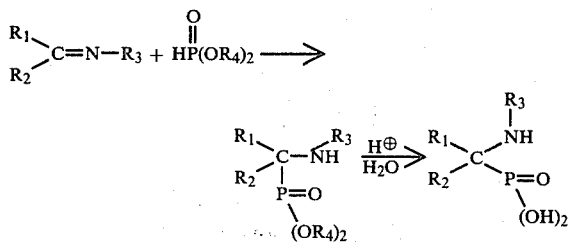

(b) Reaction of an imine formed in situ from a carbonyl compound and an amine in presence of a diester of phosphorous acid, followed by hydrolysis according to the following equation:

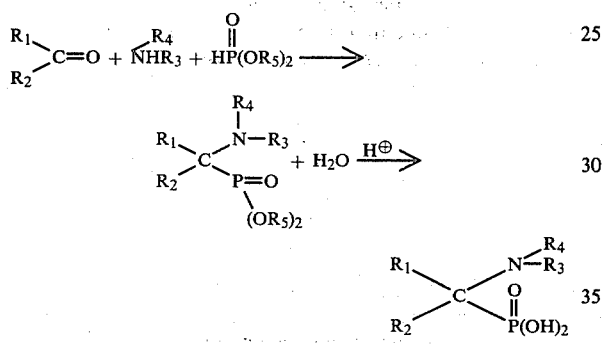

(c) Reaction of an amine with formaldehyde and phosphorous acid in presence of a large excess of strong acid (e.g. HCl) according to the following equation:

$$R_1NH_2 + HCHO + H_3PO_3 \xrightarrow{HCl} R_1-N\left[CH_2\overset{O}{\underset{\|}{P}}(OH)_2\right]_2$$

I have found unexpectedly that phosphorous acid reacts directly with imines to form α-aminophosphonic acids according to the following equation:

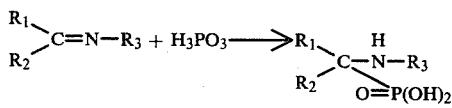

This has advantages over procedures (a) and (b) above in that not only is a single step involved but phosphorous acid is also a cheaper reactant. This procedure has significant advantages over procedure (c) since (c) works readily only when the carbonyl reactant is formaldehyde and requires an excess of strong acid. The novel procedure disclosed herein is applicable to imines derived from a wide range of carbonyl compounds and amines.

The reaction is carried out by reacting a preformed imine or an imine formed in situ with phosphorous acid under conditions capable of forming α-amino phosphonic acid. In general, the reaction is carried out by reacting substantially stoichiometric ratios of imine and phosphorous acid at temperature below the decomposition point of reactants and products. In practice, the reaction is carried out at a temperature of from about 60° C. to 250° C., such as from about 70° to 200° C., for example from about 80° to 180°, but preferably from about 95° to 170° C.

In general, any compound containing an imine group can be reacted according to this invention, for example an imine of the formula

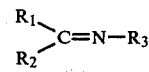

where the R's, which may be the same or different, are alkyl, aryl, cycloalkyl, alkaryl, aralkyl, heterocyclic, etc. In addition $R_1$ and $R_2$ may be joined to form a cyclic group, for example

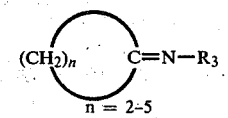

such as cyclopentyl, cyclohexyl, etc.

In addition, the imine group may be part of a ring structure, for example

for example in heterocyclic amines, for example in the following Δ'-piperidine, Δ'-pyrroline, 3,4-dihydroisoquinoline, 3,4-dihydroquinoline.

In addition, "masked" imines can also be reacted, i.e., compounds which convert to imines during reaction, for example triazines such as hexahydrotriazine

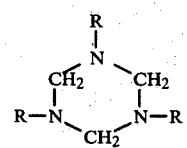

where R is a substituted group such as alkyl, etc.; linear amines such as

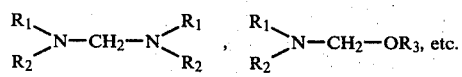

where $R_1$ and $R_2$ are alkyl or cycloalkyl.
cyclic amines such as

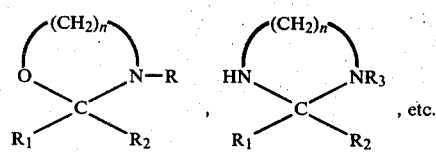

when n=2-3
where the R's are hydrogen, or a substituted group; etc.

In addition, the reaction may be carried out with polyimines derived from polyamines for example $$\underset{R_2}{\overset{R_1}{>}}C=N-A-N=C\underset{R_2}{\overset{R_1}{<}},$$

where A is alkylene, etc.

$$\underset{R_2}{\overset{R_1}{>}}C=N-Ar-N=C\underset{R_2}{\overset{R_1}{<}}$$

where Ar is an aryl group such as phenylene, substituted phenylene, etc.

Imines can be formed from carbonyl compounds, aldehydes and ketones, and primary amines.

See for example "The Chemistry of the Carbon Nitrogen Double Bond," S. Patai, Editor, *Interscience Publishers*, 1970, pages 61–148.

"The Chemistry of Imines," R. W. Layer, *Chemical Reviews*, Vol. 63, 489–510 (1963).

The following are examples of carbonyls such as aldehydes and ketones which can be reacted with amines to form imines which are useful in reacting with phosphorous acid to form α-aminophosphonic acids.

Any suitable aldehyde can be employed, i.e., any aldehyde having a $$\overset{O}{\underset{}{\overset{\|}{-CH}}}$$

group. This includes aldehydes of the formula $$\overset{O}{\underset{}{\overset{\|}{R\ CH}}}$$

where R is alkyl, aryl, cycloalkyl, alkaryl, aralkyl, heterocyclic, etc. R is alkyl or aryl for example having from 1 to 30 or more carbons, such as from 1 to 18 carbons but preferably from 1–12 carbons. These include for example acetaldehyde, propionaldehyde, butyraldehyde, heptaldehyde, etc., as well as substituted aldehydes such as aldol, etc.

Non-limiting examples of aromatic aldehyde are as follows:
Benzaldehyde
2-methylbenzaldehyde
3-methylbenzaldehyde
4-methylbenzaldehyde
2-methoxybenzaldehyde
4-methoxybenzaldehyde
α-Naphthaldehyde
β-Naphthaldehyde
4-phenylbenzaldehyde Also included are polyaldehydes such as those of the general formula $$R\left(\overset{O}{\underset{}{\overset{\|}{CH}}}\right)_n$$

where R is alkylene, cycloalkylene, arylene, heterocyclic, etc., for example of the general formula $$\overset{O}{\underset{}{\overset{\|}{HC}}}-(CH_2)_n-\overset{O}{\underset{}{\overset{\|}{CH}}}$$

where n=1–8 of more, for example succinaldehyde, etc.

Also included are arylpolyaldehydes such as those of the general formula $$\overset{O}{\underset{}{\overset{\|}{HC}}}-\underset{}{\overset{}{\bigcirc}}-\overset{O}{\underset{}{\overset{\|}{CH}}}$$

or isomers or substituted derivatives thereof, etc.

Ketones may also be employed herein in place of aldehydes. Thus, the formula aldehyde $$\overset{O}{\underset{}{\overset{\|}{RC\ H}}} \text{ may be } \overset{O}{\underset{}{\overset{\|}{R\ C\ R}}} \text{ (ketone)}$$

where the R groups, which may be the same or different, are those specified herein such as alkyl, cycloalkyl, aryl, heterocyclic, or the R's may be joined into a ring structure such as $$\overset{O}{\underset{}{\overset{\|}{\underset{\bigcirc}{C}}}}$$

where the ring structure is cycloalkyl for example cyclohexanone, etc.

Any suitable primary amine can be employed. These include compounds of the formula R—NH$_2$, where R is a substituted group preferably a hydrocarbon group, for example alkyl, cycloalkyl, alkenyl, heterocyclic, substituted derivatives of the above, etc.

ALKYL

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, etc. having 1–50 or more carbons, such as 1–30, but preferably 12–18 carbons.

The term "alkyl" also includes isomers of the straight chain group wherein branching occurs along the chain, for example $$CH_3-\underset{\underset{CH_3}{|}}{\overset{\overset{CH_3}{|}}{C}}-CH_2-NH_2; \quad CH_3-\underset{\underset{H}{|}}{\overset{\overset{CH_3}{|}}{C}}-\underset{\underset{H}{|}}{\overset{\overset{CH_3}{|}}{C}}-CH_2-NH_2;$$

$$CH_3-(CH_2)_{10}-\underset{\underset{NH_2}{|}}{\overset{\overset{H}{|}}{C}}-CH_3; \text{ etc.}$$

ALKENYL

These include unsaturated analogues (for example, 2–50, such as 2–30 carbon atoms) of alkyl groups containing one or more —C=C— groups, for example, decenyl, dodecenyl, tridecenyl, tetradecenyl, pentadecenyl, hexadecenyl, heptadecenyl, octadecentyl, etc., dienes for example octadienyl, etc., trienes, for example octatrienyl, etc.

CYCLOALKYL

These include:

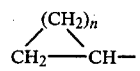

for example cyclobutyl, cyclopentyl, cyclohexyl, cycloheptyl, cyclooctyl, etc.; substituted derivatives thereof, for example alkyl or polyalkyl, for example alkyl cyclohexyl, dialkyl cyclohexyl, etc.

The following are examples of commercial amines. The nomenclature of such amines is derived from either their chain length or source of raw materials, for example, Armeen 8D-Octyl amine
Armeen C-Coconut oil amine
Armeen S-Soybean oil amine
Armeen T-Tallow amine
Armeen O-Oleyl amine
Armeen HT-Hydrogenated tallow amine Products with "D" designate distilled grade. Products without "D" designate technical grade.

Polyamines containing more than one primary amine can be employed such as contain 2 or more primary amines, provided all amine groups are converted to imines. Examples of diamines are of the general formula $NH_2-A-NH_2$ where A is alkylene, for example having 1-10 or more carbons, for example
$NH_2CH_2CH_2CH_2NH_2$
$NH_2CH_2CH_2CH_2CH_2NH_2$
1-6-hexamethylenediamine
1-10-decamethylenediamine Other suitable amines are exemplified by:

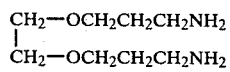

1-2-diaminocyclohexane
Di(2-aminoethyl) ether
Di(2-aminoethyl) sulfide

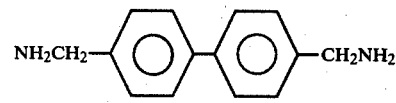

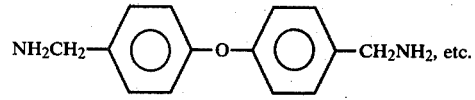

An example of a polyamine containing more than two primary amine groups is pentaerythrityltetramine, etc.

It should be noted that Hydroxylamine can also be employed such as alkanol amines, for example ethanolamine, etc.

However, it should be noted that masked imines such as oxazolidine

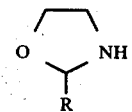

yields imines of hydroxylamine in situ and is thus equivalent to

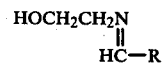

The following are non-limiting examples of ring system containing $-N=C$ groups:

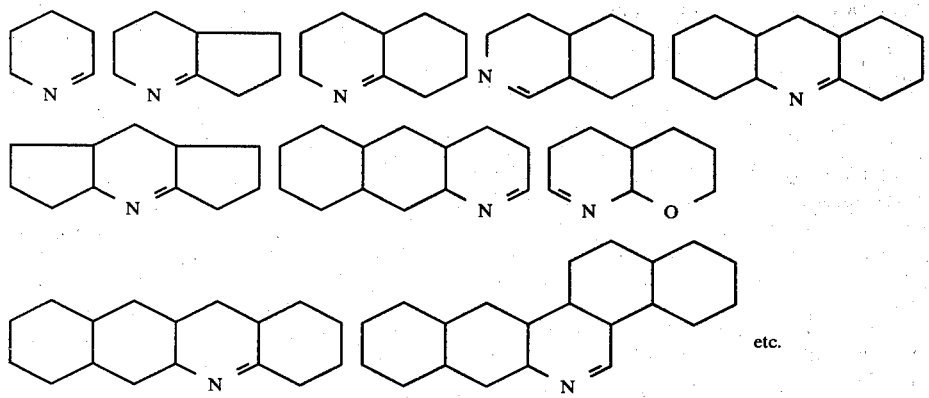

etc.

The above ring systems may also be substituted. The adjacent rings may also contain heterocyclic groups for example oxygen, nitrogen, etc., and/or may contain rings having less than six molecules in the ring for example a 5 member ring.

In certain instances more than one nitrogen group may be capable of reacting with $H_3PO_4$ so that phosphonic substitution may occur in more than one ring.

Generally, the ring system is a hydroaromatic system, i.e., where the original aromatic structure is hydrogenated, for example as illustrated in the following:

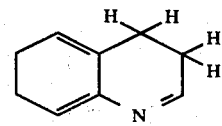

-continued

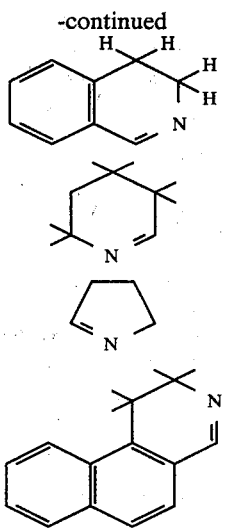

In addition, the reaction can be carried out with polymeric imines, for example those of the general formula

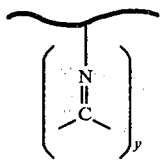

Polymer Backbone or copolymers thereof.

The following examples are presented for purposes of illustration and not of limitation.

EXAMPLE 1

Preparation of N-benzyl α-aminobenzylphosphonic acid

The imine from benzaldehyde and benzylamine (65 g; 0.33 mole) was added to phosphorous acid (27.3 g; 0.33 mole) and the mixture stirred with heating. As the temperature reached 95°–100° the whole mixture became a homogeneous liquid which reacted vigorously as the temperature reached 115°–120°. The reaction mass became very viscous and was allowed to cool to a glass. This glass was dissolved in aqueous sodium carbonate and upon acidification gave N-benzyl α-aminobenzylphosphonic acid, mp 233°–4°, 90 g.

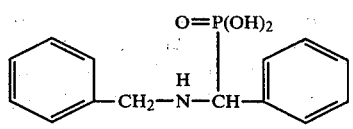

Analysis: Calculated for $C_{14}H_{16}NO_3P$; N, 5.05; P, 11.18 Found N, 4.91; P, 11.05

EXAMPLE 2

N-benzyl α-amino p-chlorobenzylphosphonic acid

A mixture of the imine of p-chlorobenzaldehyde and benzylamine (44 g) and phosphorous acid (15.7 g) was heated with stirring. The mixture became liquid and homogeneous at 75°–80° and at 100°–115° reaction commenced raising the temperature to 140°–150°. Upon cooling the reaction mass set to a glass which was dissolved in aqueous sodium carbonate solution. Addition of hydrochloric acid precipitated a white solid which upon drying yielded N-benzyl α-amino p-chlorobenzylphosphonic acid, mp 226°–30°, 52 g.

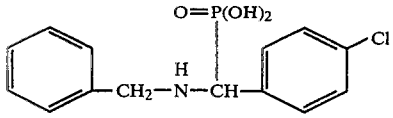

Analysis: Calculated for $C_{14}H_{15}ClNO_3P2H_2O$; N, 4.03; P, 8.92. Found: N, 3.93; P, 8.55.

EXAMPLE 3

N-methyl α-aminobenzylphosphonic acid

Phosphorous acid (13.9 g; 17 mole) and N-benzylidene methyl amine (20.1 g; 0.17 mole) were heated together with stirring. As the temperature of the reaction mixture reached 100°–110° an exothermic reaction took place. As the viscous product cooled to 95°–8° water was added resulting in the formation of white crystals. The mixture was cooled and filtered to yield pure N-methyl α-aminobenzylphosphonic acid.

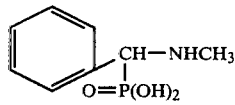

Analysis: Calculated for $C_8H_{12}NO_3P$: N, 6.97; P, 15.42 Found: N, 7.07; P, 15.52
Nmr was entirely consistent with the structure showing peaks δ, 2.63 (N—CH$_3$), 4.05 (CH) 7.50 (phenyl).

EXAMPLE 4

Addition of a cyclic imine. Preparation of tetrahydroisoquinoline-1-phosphonic acid.

A mixture of 3,4-dihydroisoquinoline (13.6 g) and phosphorous acid (8.5 g) was heated with stirring. The mixture underwent a vigorous exothermic reaction as the temperature reached 105°. After maintaining the mixture at 100°–105° for 1 hour water (30 ml) was added to dissolve the yellow gum. Upon cooling pale yellow needles separated mp 256°–8° of the formula

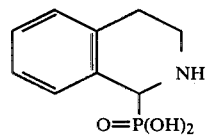

Analysis: Calculated for $C_9H_{11}NO_3P$; N, 6.60; P, 14.62. Found: N, 6.30; P, 14.74.

EXAMPLE 5

N-ethyl α-amino benzylphosphonic acid

N-benzylidene ethylamine (13.4 g; 0.1 mole) and phoshporous acid (8.2 g; 0.1 mole) were heated with stirring at 150° for 30 minutes. Upon cooling the reaction mass was dissolved in water (20 ml). Addition of ethanol precipitated the product as white needles mp 225°–8°, 14.7 g of the formula

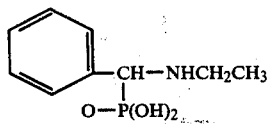

Analysis: Calculated for $C_9H_{14}NO_3P$; N, 6.52; P, 14.40 Eq. wt. 215 Found: N, 6.13; P, 14.47 Eq. wt. 217.

EXAMPLE 6

N-ethyl α-amino methylphosphonic acid

Phosphorous acid (26.5 g) was warmed to 70° (melt) and while stirring 1,3,5-triethyl hexahydrotriazine (18.5 g) was added dropwise in 20 minutes. No cooling was applied and the reaction temperature reached 160°. After cooling, water was added to dissolve the gum. The aqueous solution was basified and extracted with chloroform. The aqueous portion was passed through an ion exchange resin (Dowex 50W). Evaporation of the eluate yielded N-ethyl α-aminomethylphosphonic acid.

Nmr showed peaks at 1.30 (triplet), 3.08 (quartet) 3.30 (doublet).

This is consistent with the structure

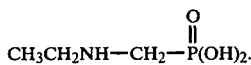

EXAMPLE 7

To the imine from isobutyraldehyde and benzylamine (51.4 g; 0.3 mole) was added phosphorous acid (24.6 g; 0.3 mole). While stirring the mixture was slowly warmed to 65°-70° when a vigorous exothermic reaction was initiated. The reaction temperature reached 130°-145°. Upon cooling the reaction mixture became a glass. This glass was dissolved in water and basified. Extraction with benzene yielded benzylisobutylamine. The aqueous portion was acidified and after removal of sodium chloride yielded a phosphonic acid (20 g). Recrystallization gave a white solid (12 g) mp 186°-190° the N-benzyl α-aminophosphonic acid.

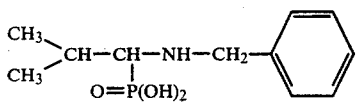

Anal: Calcd. for $C_{11}H_{18}NO_3P$: N, 5.76; P, 12.76 Found N, 5.07; P, 12.26.

Phosphorus nmr gave a peak at −10.7 ppm (relative to 85% $H_3PO_4$) consistent with the structure.

EXAMPLE 8

An oxazolidine of the formula

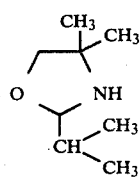

was prepared from 2-amino-2-methyl-1-propanol and isobutyraldehyde. To this oxazolidine (17.1 g; 0.12 mole) was added phosphorous acid (9.8 g; 0.12 mole). While stirring and heating gently the reactants underwent a vigorous exothermic reaction. After heating at 130° for 1 hour the reaction mixture was cooled to 85° and water added. The aqueous solution was extracted with benzene and then evaporated to yield a glass. Careful crystallization gave the phosphonic acid mp 260°-2° (with decomposition). Phosphorus nmr showed a peak at −7.7 ppm (relative to 85% $H_3PO_4$) consistent with the phosphonic acid of the formula

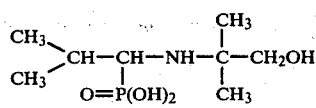

EXAMPLE 9

To the imine derived from salicylaldehyde and benzylamine (34.8 g; 0.165 mole) was added phosphorous acid (13.5 g; 0.165 mole) and the mixture heated and stirred. As the temperature reached 50° the reaction became very fluid and upon reachingg 90° an exothermic reaction ensued raising the temperature rapidly to 140°. The reaction mixture which became quite viscous was held at 135°-140° for 40 minutes and then cooled to 90°. Water was added. Basification and extraction yielded a basic produce (12.5 g). The aqueous phase was acidified to precipitate a gummy solid. Dissolution of this solid in base and reprecipitation gave pure phosphonic acid as a pale yellow solid. (11.0 g) of the formula

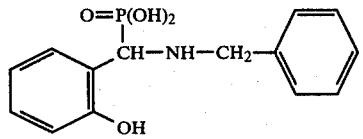

EXAMPLE 10

Use of pyridine as a solvent.

The imine from benzaldehyde and benzylamine (19.5 g; 0.1 mole) was dissolved in pyridine (9 g) and phosphorous acid (8.2 g; 0.1 mole) was added. The mixture was heated at reflux for 3 hours, cooled, basified and extracted with benzene. The residue was acidified to yield a white solid. Crystallization gave N-benzyl α-amino benzylphosphonic acid mp 233°-4°. Phosphorus nmr of a basified aqueous solution gave a peak at −15.9 ppm (relative to 85% $H_3PO_4$) consistent with the assigned structure given in Example 1.

The compositions of this invention have a wide variety of uses, for example such as
Scale inhibitors,
Corrosion inhibitors, particularly in acids and aerated brines,
Chelating agents,
Biocides, etc.

I claim:

1. A process of preparing α-amino phosphonic acids which consists essentially of reacting an oxazolidine with phosphorous acid, in substantially stoichiometric ratios at temperatures below the decomposition point of the reactants and products.

2. The process of claim 1 where the temperature of the reaction is from 60° C. to 250° C.
3. The process of claim 1 where the oxazolidine reacted has the formula
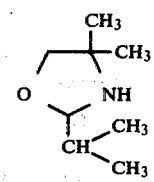
4. The process of claim 1 where the oxazolidine and the phosphorous acid are the only reactants present.
* * * * *